United States Patent [19]

Harvill et al.

[11] Patent Number: 5,097,252
[45] Date of Patent: Mar. 17, 1992

[54] MOTION SENSOR WHICH PRODUCES AN ASYMMETRICAL SIGNAL IN RESPONSE TO SYMMETRICAL MOVEMENT

[75] Inventors: Young L. Harvill, Palo Alto; Thomas G. Zimmerman, San Francisco; Jean-Jacques G. Grimaud, Palo Alto, all of Calif.

[73] Assignee: VPL Research Inc., Redwood City, Calif.

[21] Appl. No.: 427,970

[22] Filed: Oct. 26, 1989

Related U.S. Application Data

[63] Continuation of Ser. No. 29,934, Mar. 24, 1987, abandoned.

[51] Int. Cl.⁵ .................................................. G01B 5/34
[52] U.S. Cl. .............................. 340/540; 200/DIG. 2; 340/407; 340/600; 250/227.14; 250/227.16; 250/227.24; 250/227.28; 73/655; 341/20; 341/31; 385/13
[58] Field of Search .......................... 341/20, 21, 31; 340/407, 600, 540, 825.19, 555-557; 250/551, 221, 227.14, 227.16, 227.24, 227.28; 434/112, 229; 350/96.1, 96.15, 96.29; 200/DIG. 2; 73/763, 774, 775, 800, 655, 768

[56] References Cited

U.S. PATENT DOCUMENTS

| | | | |
|---|---|---|---|
| 1,335,272 | 3/1920 | Broughton | 200/DIG. 2 |
| 3,777,086 | 12/1973 | Riedo | 200/DIG. 2 |
| 4,408,495 | 10/1983 | Couch et al. | 250/227 |
| 4,414,537 | 11/1983 | Grimes | 340/365 P |
| 4,524,348 | 6/1985 | Lefkowitz | 340/365 R |
| 4,542,291 | 9/1985 | Zimmerman | 250/551 |
| 4,613,139 | 9/1986 | Robinson, II | 200/DIG. 2 |
| 4,634,856 | 1/1987 | Kirkham | 250/227 |
| 4,654,520 | 3/1987 | Griffiths | 73/800 |
| 4,660,033 | 4/1987 | Brandt | 340/365 R |
| 4,665,388 | 5/1987 | Ivie et al. | 200/DIG. 2 |
| 4,715,235 | 12/1987 | Fukui et al. | 73/775 |
| 4,905,001 | 2/1990 | Penner | 341/20 |

Primary Examiner—Jin F. Ng
Assistant Examiner—Jill Jackson
Attorney, Agent, or Firm—Townsend and Townsend

[57] ABSTRACT

In one embodiment of the invention, a plurality of sensors are placed over the joints of a hand. Each motion sensor comprises an optical fiber disposed between a light source and a light sensor. An upper portion of the fiber is treated so that transmission loss of light being communicated through the optical fiber is increased only when the fiber bends in one direction. In another embodiment of the invention, a flexible tube is disposed in close proximity to a finger joint and bends in response to bending of the finger. A light source and light sensor are provided on opposite ends of the tube for continuously indicating the extent of bending of the tube. A wedge is disposed between the tube and the finger for setting the tube straight when the finger is hyperextended for eliminating the symmetry of the output signal which ordinarily would result from bending of the tube on opposite sides of the axis of movement. In a further embodiment of the invention, a light source and light sensor are positioned in close proximity to a finger joint so that bending of the finger toward the palm causes the source and sensor to move away from each other. Bending the finger in the opposite direction causes the source and sensor to move toward each other.

36 Claims, 6 Drawing Sheets

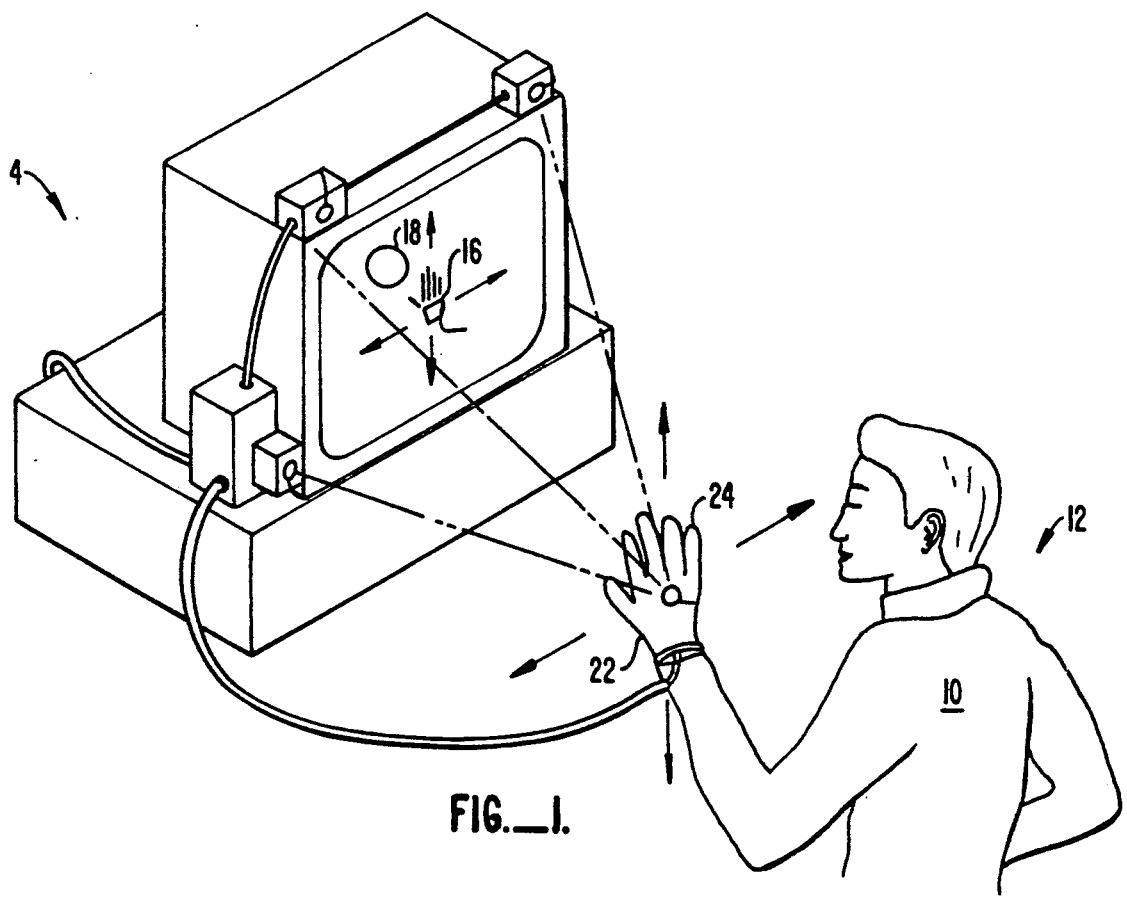
FIG._1.
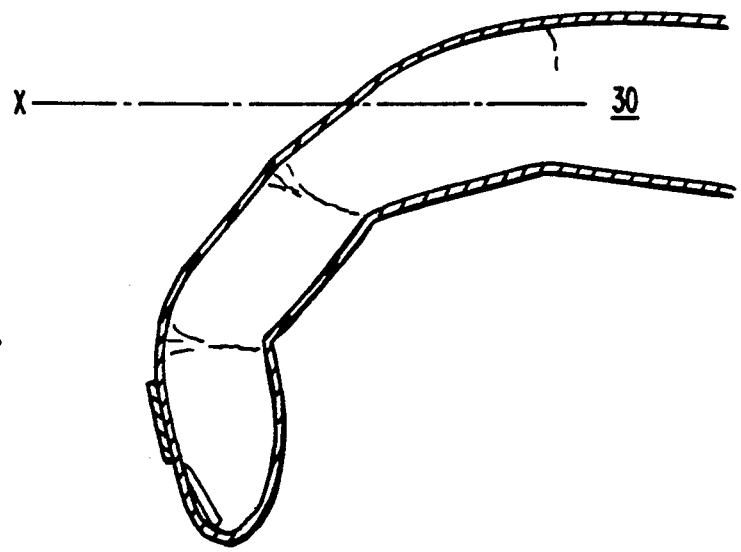
FIG._2.
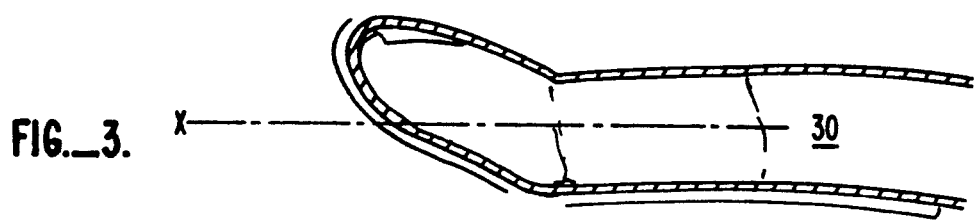
FIG._3.

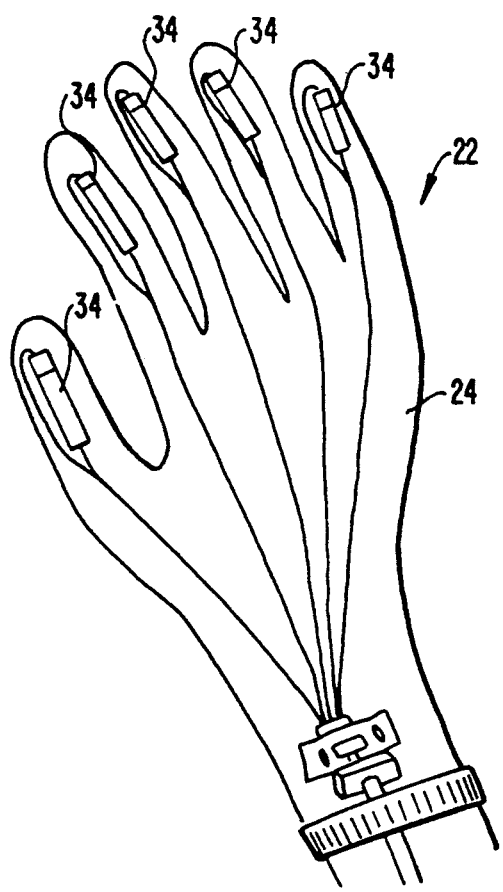
FIG._4A.
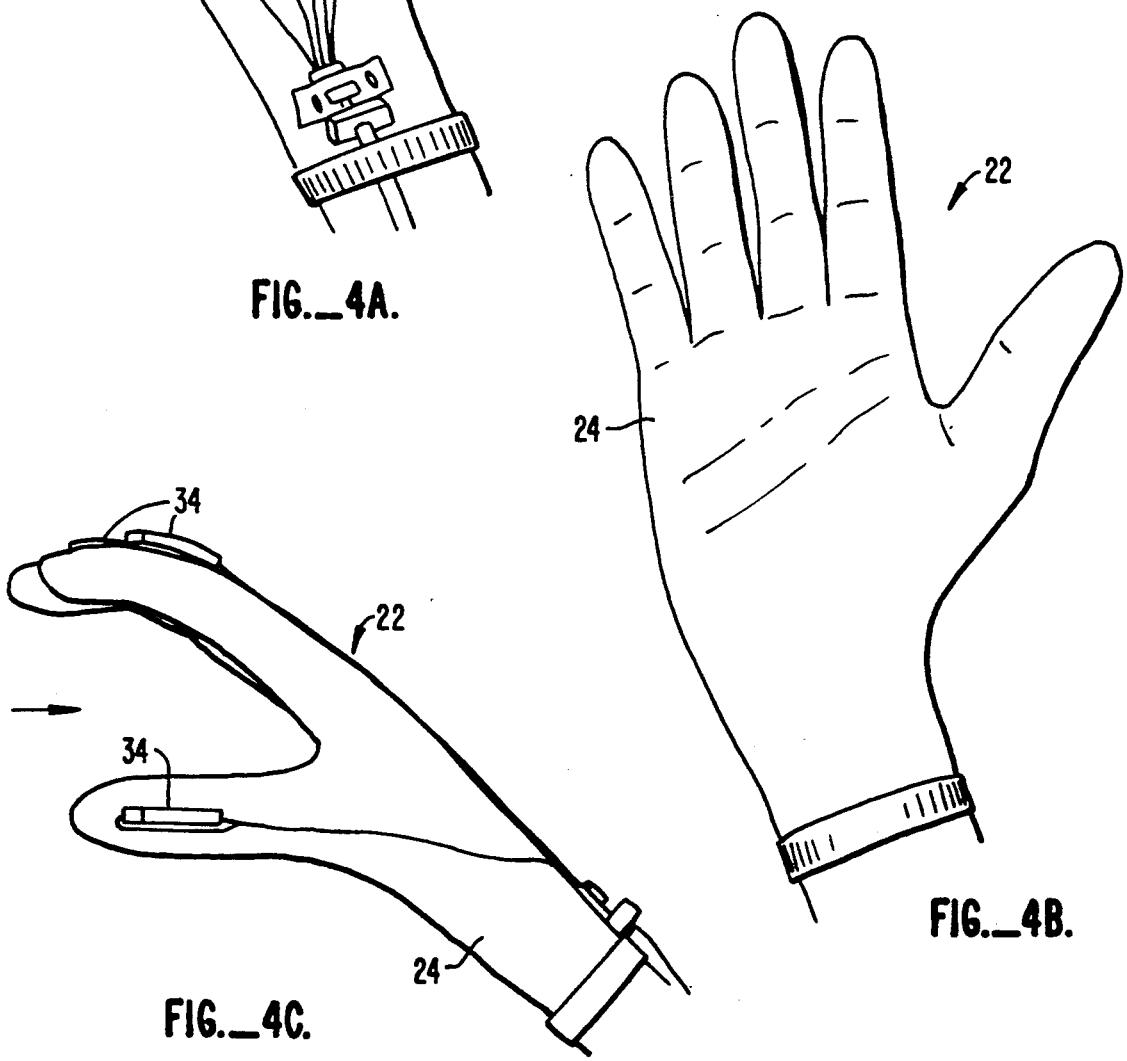
FIG._4B.
FIG._4C.

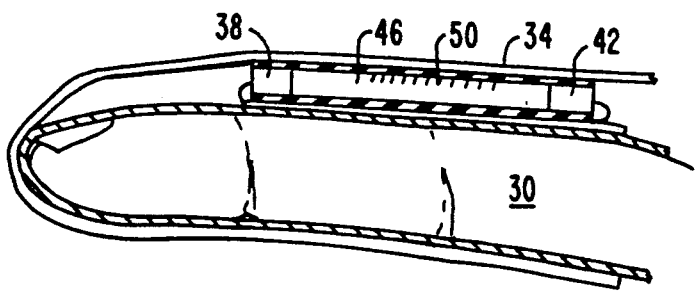
FIG._5.
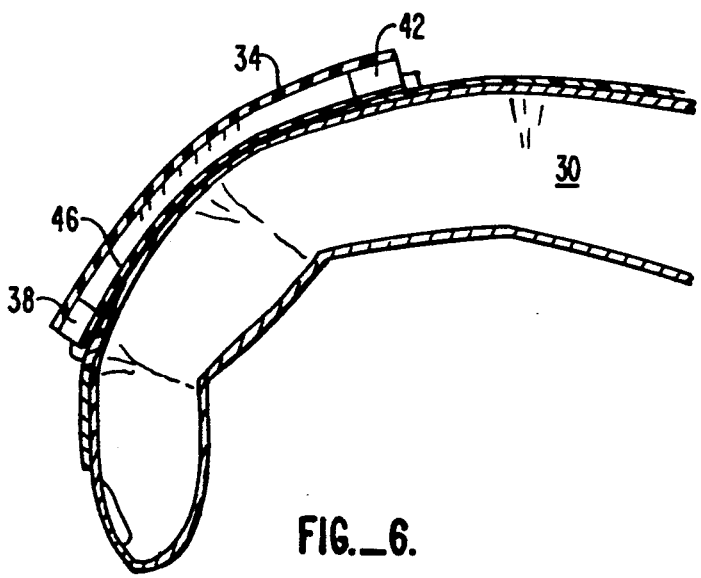
FIG._6.
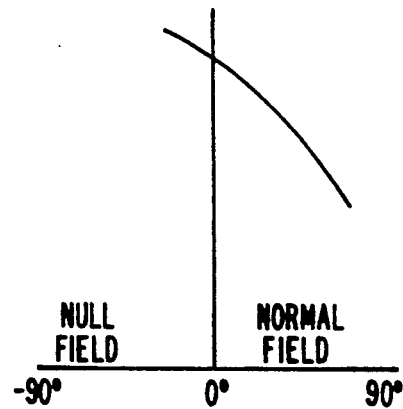
FIG._10.
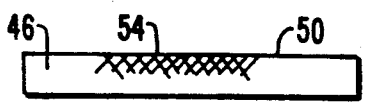
FIG._7A.
FIG._8A.
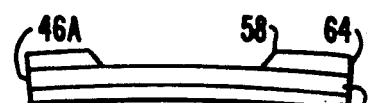
FIG._9A.
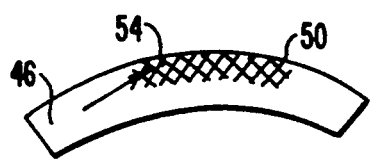
FIG._7B.
FIG._8B.
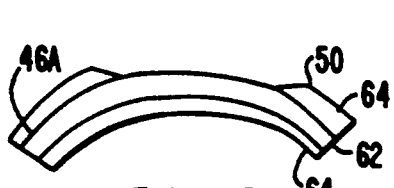
FIG._9B.

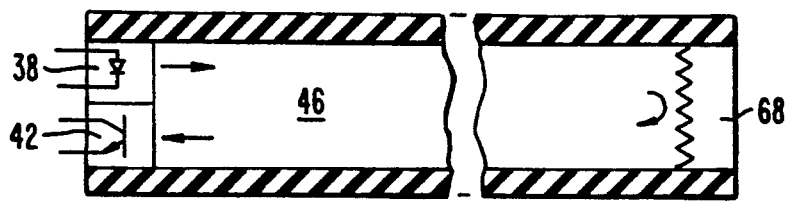
FIG._11.
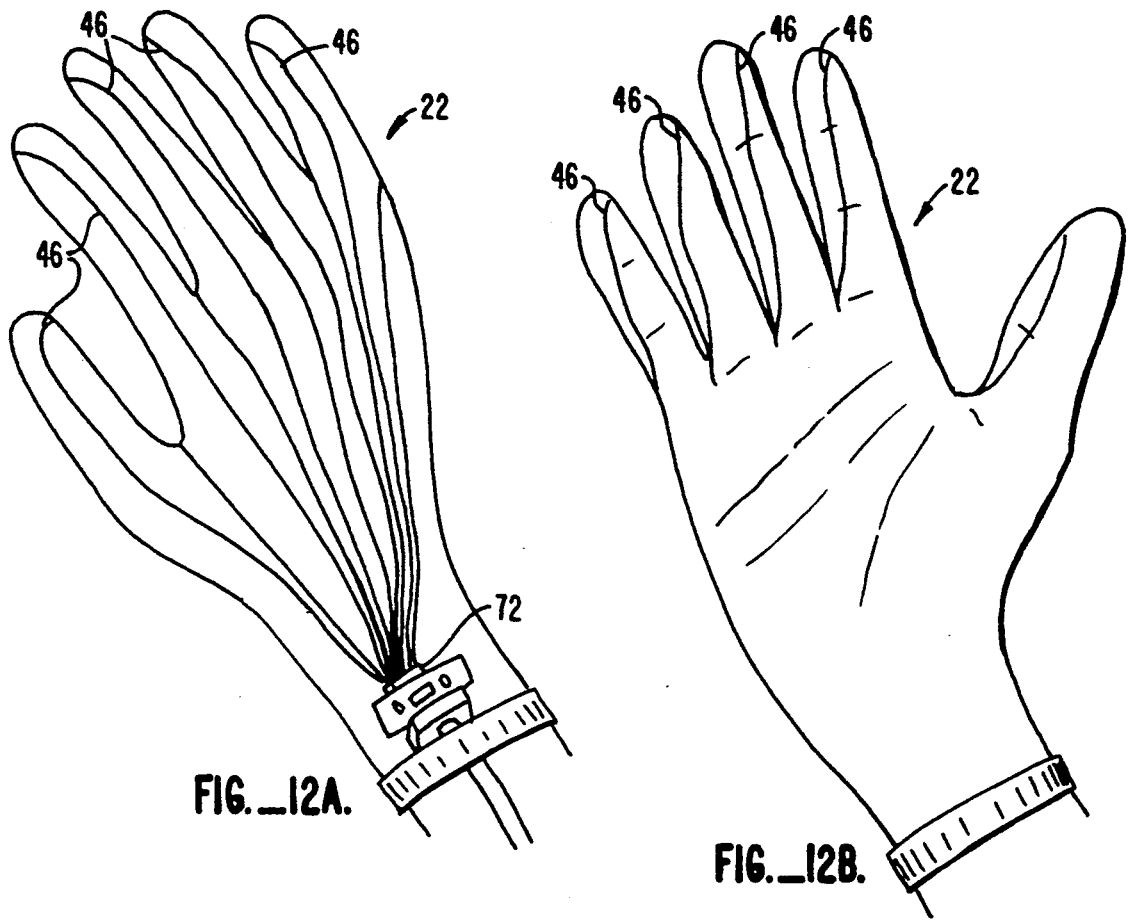
FIG._12A.
FIG._12B.
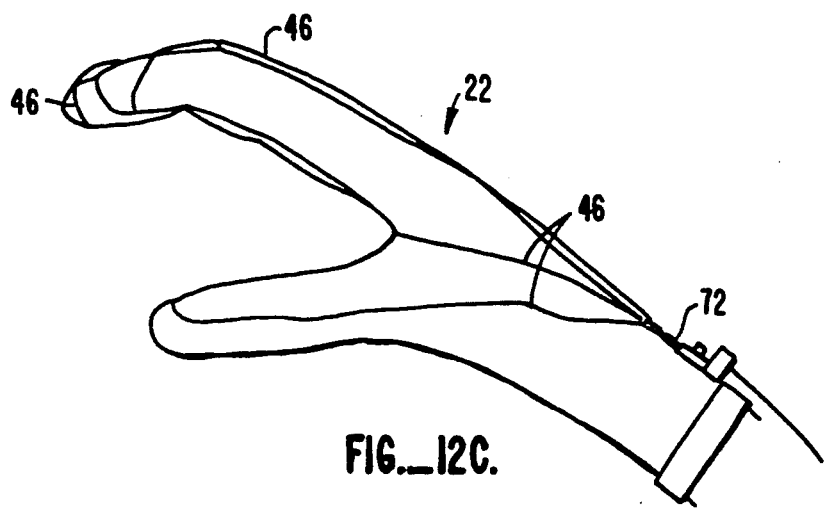
FIG._12C.

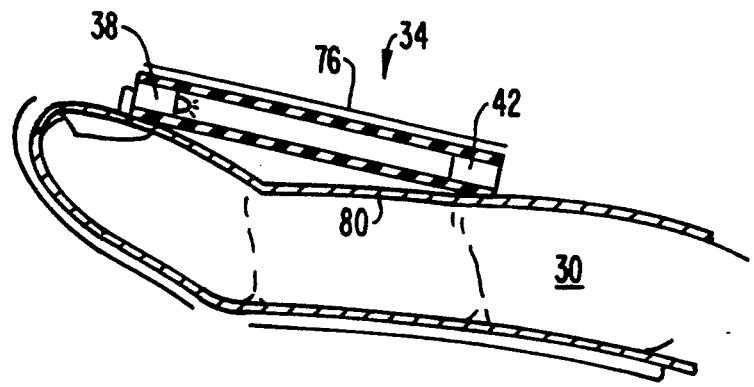
FIG._13.
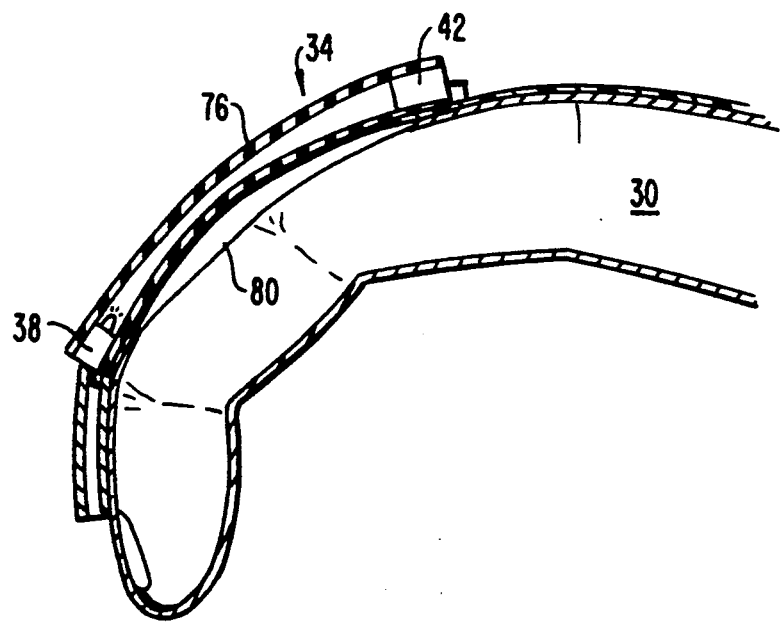
FIG._14.

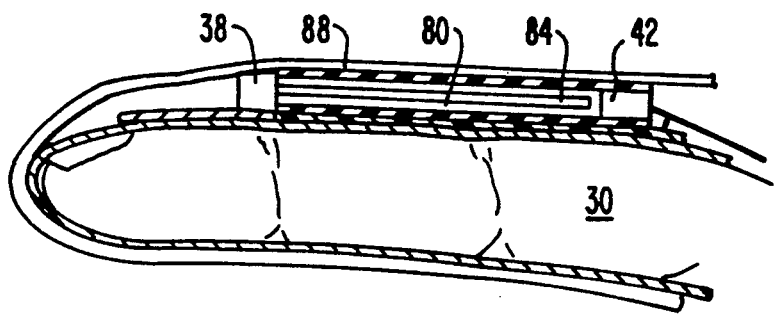
FIG._15.
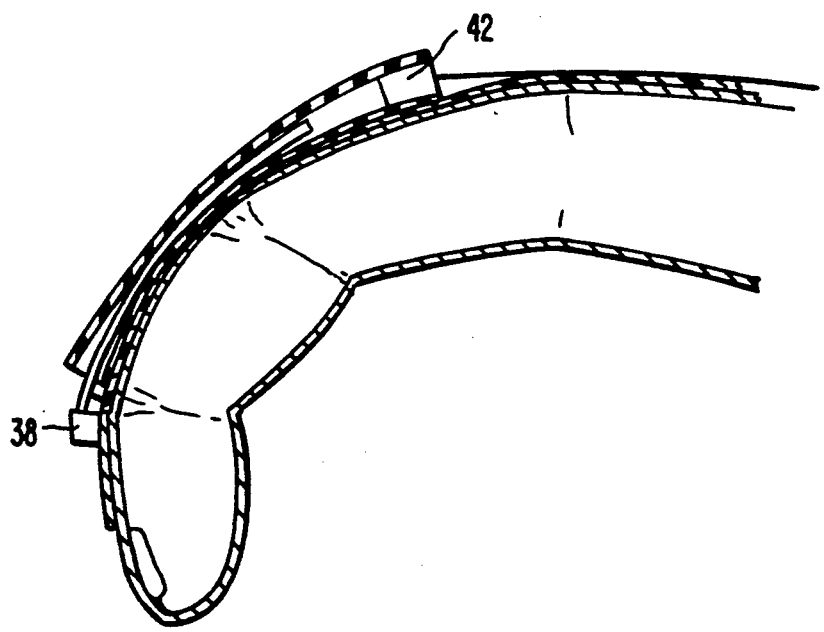
FIG._16.

MOTION SENSOR WHICH PRODUCES AN ASYMMETRICAL SIGNAL IN RESPONSE TO SYMMETRICAL MOVEMENT

This is a continuation of application Ser. No. 07/029,934, filed Mar. 24, 1987, now abandoned.

BACKGROUND OF THE INVENTION

1. Field of the Invention

This invention relates to motion sensors and, more particularly, to a motion sensor disposed in close proximity to a physical body and which produces an asymmetrical output signal in response to symmetrical movement of the body.

2. Description of the Relevant Art

Many input devices are used to input data to machines. For example, keyboards, joysticks, mice, track balls, and light pens often are used to input data into a computer, usually so that operations may be selected without the necessity of keying in multiple commands on a keyboard. However, mastering the operation of such input devices is often difficult because the hand movements required to operate the device do not correspond to the visual feedback presented by the display screen of the computer.

One method and apparatus which overcomes the foregoing disadvantage is described in U.S. patent application Ser. No. 07/026,930, entitled "Computer Data Entry And Manipulation Apparatus And Method," filed on Mar. 17, 1988, now abandoned and assigned to the present assignee. That application discloses a data processing apparatus for converting gestures and positions of the hand of a physical operator into a virtual operator, such as an animated version of the hand, for manipulating virtual objects defined by a computer.

In order to accomplish the translation from the gestures and movements of the physical operator into corresponding gestures and movements of a virtual operator, flex sensors are disposed in close proximity to the physical operator for producing an output signal in response to movement of the operator's body. One example of such a flex sensor is disclosed in U.S. Pat. No. 4,542,291, issued to Thomas G. Zimmerman and assigned to the present assignee. In the embodiments disclosed, the sensors are placed on a glove for detecting the movements and gestures of the hand of the operator. Each sensor comprises a flexible tube having two ends, a reflective interior wall within the flexible tube, and a light source placed within one end of the flexible tube. A photosensitive detector placed within the other end of the flexible tube measures the amount of direct and reflected light received from the light source as the tube is bent.

Another input device used for a somewhat different purpose is described in U.S. Pat. No. 4,414,537, issued Nov. 8, 1983, to G. Grimes, entitled "Digital Data Entry Glove Interface." The Grimes patent discloses a glove with sensors for detecting the flexing of finger joints, sensors for detecting contact between various portions of the hand, and sensors for detecting the orientation of the hand. The Grimes device is used for translating discrete hand positions representing alphanumeric characters into corresponding electrical signals.

Although the foregoing devices visually operate satisfactorily, the sensors used may give erroneous information in certain circumstances. For example, if sensors are positioned to detect bending at a junction of two members which pivot symmetrically with respect to an axis, but only movement on one side of the axis provides usable data, the computer may be unable to determine if the output produced by the sensors correspond to movement in the desired direction. That is, the sensors provide the same signal when the two members are in symmetrically opposite positions so that the computer may receive and process the data as if the data represented movement in the relevant direction when, in fact, that is not the case. Consequently, the computer is unable to translate the movements of the operator into the proper form, or the translation is performed incorrectly and the results are meaningless.

SUMMARY OF THE INVENTION

The present invention is directed to a motion sensor for measuring movement of a physical body which moves symmetrically with respect to a boundary. The motion sensor monitors movement of the body and provides an asymmetrical output signal in response to the symmetrical movement of the body. In one embodiment of the present invention, a plurality of motion sensors are placed over the joints of a hand and provide an asymmetrical output signal which indicates the direction of movement of the hand. To avoid providing incorrect data when a part of the hand, e.g., a finger, is hyperextended, the motion sensors comprise an optical fiber disposed between a light source and a light sensor. An upper portion of the optical fiber is treated, e.g., by abrasion or notching, so that transmission loss of light being communicated throught the optical fiber is increased only when the fiber bends in one direction.

In another embodiment of the present invention, a flexible tube is disposed in close proximity to a finger joint and bends in response to bending of the finger. A light source and light sensor are provided on opposite ends of the tube for continuously indicating the extent of bending of the tube. A wedge is disposed between the tube and the finger for setting the tube in a prescribed orientation, e.g., straight, when the finger is in a prescribed position, e.g., hyperextended. In this manner, the symmetry of the output signal which ordinarily would result from bending of the tube on opposite sides of the axis of movement is avoided.

In a further embodiment of the invention, a light source and light sensor are positioned in close proximity to a finger joint so that bending of the finger toward the palm causes the source and sensor to move away from each other. Bending the finger in the other direction causes the source and sensor to move toward each other. A guide faces the light emitted by the source toward the sensor so that the degree of bending may be determined by the amount of light received by the sensor.

BRIEF DESCRIPTION OF THE DRAWINGS

FIG. 1 is an overall perspective view of a data processing system according to the present invention wherein movements of a part of a body of a physical operator are converted into a virtual operator for manipulating a virtual object represented in the data processing system.

FIG. 2 is a view of a finger bent in a normal direction of movement.

FIG. 3 is a view of a finger which illustrates the finger in a hyperextended position.

FIG. 4a is a back view of an instrumented glove assembly according to the present invention.

FIG. 4b is a palm-side view of the instrumented glove assembly of FIG. 4a.

FIG. 4c is a side view of the instrumented glove assembly of FIG. 4a.

FIG. 5 is a sectional detailed view of one finger of the instrumented glove assembly of FIGS. 4a, 4b, and 4c with the finger having an extended orientation.

FIG. 6 is a sectional detailed view of one finger of the instrumented glove assembly of FIGS. 4a, 4b, and 4c with the finger having a bent orientation.

FIGS. 7a and 7b are straight and bent views, respectively, of an optical fiber having an abraded upper surface.

FIGS. 8a and 8b are straight and bent views, respectively, of an optical fiber having a notched upper surface.

FIGS. 9a and 9b are straight and bent views, respectively, of a layered multimode step index optical fiber having a portion of the upper layer removed.

FIG. 10 is a view of an alternative embodiment of the invention wherein a retroreflector is fitted on the end of an optical fiber.

FIG. 11 is a graph showing light intensity as a function of movement of the finger of FIGS. 5 and 6.

FIG. 12a is a back view of an alternative embodiment of an instrumented glove assembly according to the present invention.

FIG. 12b is a palm-side view of the instrumented glove assembly of FIG. 11.

FIG. 12c is a side view of the instrumented glove assembly of FIG. 11.

FIG. 13 is a sectional detailed view of an alternative embodiment of the instrumented glove assembly disposed on a finger in a hyperextended orientation.

FIG. 14 is a sectional detailed view of the instrumented glove assembly of FIG. 13 with the finger having a bent orientation.

FIG. 15 is a sectional detailed view of an alternative embodiment of an instrumented glove assembly disposed on a finger in a hyperextended orientation.

FIG. 16 is a sectional detailed view of the instrumented glove assembly of FIG. 15 with the finger having a bent orientation.

DETAILED DESCRIPTION OF THE PREFERRED EMBODIMENTS

FIG. 1 is an overall perspective view of a data processing system 4 wherein movements of a part of the body 10 of a physical operator 12 are converted into a virtual operator 16 for manipulating a virtual object 18 represented on the display screen of data processing system 4. The movements of physical operator 12 preferably are converted into virtual operator 16 through instrumentation disposed in close proximity to a part of the body 10 of physical operator 12, preferably on the clothing of physical operator 12. For purposes of illustration, the movements of a hand 22 of physical operator 12 are converted into virtual operator 16 through a glove 24, as described in copending U.S. patent application Ser. No. 07/029,930, entitled "Computer Data Entry And Manipulation Apparatus And Method," filed on 3/14/87, now abandoned and assigned to the present assignee. It is to be understood, however, that the present invention may be employed along any part of the body of physical operator 12 which may be used for entering data into data processing system 4.

FIGS. 2 and 3 are diagrams illustrating a part of the body of physical operator 12, e.g., a finger 30, the movement of which is useful for entering data into data processing system 4. As with many parts of the body, finger 30 is capable of moving symmetrically with respect to a boundary line X. The movement on the lower side of boundary X illustrated in FIG. 2 may be termed the "normal" field of movement, since that is the direction of movement which is normally employed to manipulate an object. The movement on the other side of boundary X, depicted in FIG. 3, may be termed the "null" field of movement, the measurement of which has little or no value in some applications. If a sensor disposed on finger 30 measures only the amount of bend of finger 30 and not its direction, then there is no way of determining whether the data provided by the sensor represents movement in the normal or null field, and hence whether the data should be processed or disgarded as irrelevant.

FIGS. 4a, 4b, and 4c illustrate one embodiment of a glove assembly 24 used to enter data into data processing system 16. Glove assembly 24 contains several sensors 34 disposed next to the finger joints of the hand for responding to gestures of the hand. The software portion of data processing system 4 receives gesture-indicating data from sensors 34 and enters commands into data processing 4 according to the gestures recognized. These commands relate to the conversion of movements of the hand 22 of physical operator 12 into virtual operator 16.

FIGS. 5 and 6 illustrate one embodiment of sensor 34 for detecting movement of finger 30 in a prescribed direction. As shown therein, sensor 34 comprises a light source 38, a source of electromagnetic radiation, preferably a sensor for electromagnetic radiation, preferably a light sensor 42, and an optical fiber 46 for communicating the light emitted by source 38 to sensor 42. To increase the transmission loss of light being communicated through optical fiber 46 when the fiber is bent, the upper surface 50 thereof may be treated as shown in FIGS. 7a, 8a, and 9a. As shown in FIG. 7a, upper surface 50 has abrasions 54 disposed therein so that, when the fiber is bent as shown in FIG. 7b, a significant amount of light impinging upon abrasions 54 will be allowed to pass through upper surface 50, and hence never reach sensor 42. As shown in FIG. 8a, another technique for increasing the transmission loss through optical fiber 46 is to form upper surface 50 having a plurality of notches 58 so that, when the fiber is bent as shown in FIG. 8b, the surfaces of notches 58 substantially increase the angle of incidence of light rays impinging against upper surface 50 above the critical angle at which the light would be reflected, and hence a significant amount of light is transmitted through upper surface 50 and never reaches sensor 42. A similar effect may result by appropriate treatment of a layered multiple step index optical fiber 46 having an inner core 62 and an outer core 64 as shown in FIG. 9a. Outer core 64 preferably has a higher index of reflection than air. For increasing the transmission loss through fiber 46, the outer core 64 is removed on upper surface 50 so that air forms a boundary with core 62. Accordingly, the indices of reflection at the boundary of core 62 are brought substantially closer, and a significant amount of light impinging on the modified boundary is allowed to pass through and never reaches sensor 42.

In all three embodiments, there will be some transmission loss when the fiber is straight, as a result of light impinging on the treated upper surface. This transmission loss increases when optical fiber 46 is bent concavely downward (i.e., in the normal field of movement). On the other hand, the transmission loss decreases when optical fiber 46 is bent concavely upward (i.e., in the null field of movement) because light reflected by the lower surface of optical fiber 46 is reflected at an angle which avoids contact with the treated portion of upper surface 50. The net result is that the output from each sensor 34 resembles the graph of FIG. 10, and the signal symmetry of known sensors is avoided.

To decrease the amount of wiring required by the system, the embodiment of sensor 34 illustrated in FIG. 11 may be used. In this embodiment, light source 38 and light sensor 42 may be disposed on one side of optical fiber 46, and optical fiber 46 may have a retroreflector 68 disposed on its other end so that light emitted by light source 38 is reflected by retroreflector 68 and communicated to sensor 42 back through optical fiber 46. Still further simplicity results by using the embodiment of sensor 34 disclosed in FIGS. 12a, 12b, and 12c. As shown therein, optical fiber 46 originates and terminates at a control block 72, which contains the associated light sources 38 and light sensors 42 (not shown). Preferably, optical fiber 46 loops around each finger of hand 22, and the upper surface of optical fiber 46 is treated as hereinbefore described in the vicinity of each joint to be monitored.

FIGS. 13 and 14 disclose another embodiment of the present invention particularly well suited for a sensor constructed in accordance with U.S. Pat. No. 4,542,291. As shown therein, sensor 34 includes a light source 38 and a light sensor 42 disposed on opposite ends of a flexible tube 76 for providing a signal continuously indicative of the extent of the bending of finger 30. Tube 76 functions as a radiation conduit comprising a first medium (i.e., air) adjacent to a second medium (i.e., tube 76) wherein electromagnetic radiation propagates through the first medium and is at least in part reflected from an interface between the first medium and the second medium for maintaining the propagation of electromagnetic radiation through the first medium. To avoid signal symmetry when the finger is bent in the null field, a wedge 80 is disposed between tube 76 and finger 30 for setting the tube in a prescribed orientation when finger 30 is in a prescribed position. Preferably, wedge 80 sets tube 76 generally straight when finger 30 is positioned at the limit of movement in the null field as shown in FIG. 13. Software within data processing system 4 then may be drafted to calculate the amount of bend in finger 30 in the normal field of movement.

FIGS. 15 and 16 illustrate another embodiment of the present invention wherein a light source 38 and a light sensor 42 are positioned on finger 30 so that bending of finger 30 causes source 38 and sensor 42 to move relative to each other. Preferably, the light emitted by source 38 should always face sensor 42 when source 38 and sensor 42 move relative to each other to facilitate measurements. This may be accomplished, for example, by connecting an optical fiber 80 to one of source 38 or sensor 42, preferably source 38, so that a free end 84 of optical fiber 80 faces the other source or sensor, preferably sensor 42. The free end 84 of optical fiber 80 then may be disposed within a guide, preferably a flexible tube 88, so that the light emitted by source 38 will face sensor 42 when source 38 and sensor 42 move relative to each other. Tube 88 preferably is connected to the source or sensor located proximate to the free end 84 of optical fiber 80 to enhance reliability of the guiding function. When this embodiment is in operation, light emitted by source 38 will be detected by sensor 42 as it is emitted from the free end 84 of optical fiber 80. If finger 30 bends in the normal field of movement, e.g., downward, then free end 84 of optical fiber 80 moves away from sensor 42, and hence the light detected by sensor 42 decreases in intensity. On the other hand, when finger 30 moves in the null field, the free end 84 of optical fiber 80 moves closer to sensor 42 until it touches sensor 42 and the intensity of light received by sensor 42 remains the same. As a result, signal symmetry again is eliminated.

While the above is a complete description of a preferred embodiment of the present invention, various modifications are obvious to those skilled in the art. For example, the upper surface of optical fiber 46 in FIGS. 5 and 6 may be treated in any way which increases the transmission loss through the upper portion of the fiber, such as by scraping, index matching through paint or other coating, etching with acid, eccentric scoring, and by deformation of the upper surface through laser, heat, or ultrasonic methods. The embodiment of sensor 34 disclosed in FIGS. 15 and 16 may be used by encircling the sensor around the torso of the body to measure expansion and contraction of the torso as a result of inhalation and exhalation. Furthermore, optical fiber 80 in these embodiments may be eliminated, and light source 38 may be disposed on a track which maintains source 38 facing sensor 42. Consequently, the description should not be used to limit the scope of the invention which is properly described in the claims.

We claim:

1. A motion sensor comprising:
   a signal source for emitting light;
   a signal sensor for sensing the light from the signal source, the signal source and signal sensor being positioned over a joint of a body which pivots symmetrically in a plane with respect to an axis, and the signal sensor ordinarily providing a symmetrical output signal indicating the continuous extent of movement of the body in the plane when the body pivots symmetrically relative to the axis in the plane;
   asymmetrical signal means, associated with the signal source and signal sensor, for causing the signal sensor to emit an asymmetrical output signal indicating movement in the plane in response to symmetrical pivoting of the body relative to the axis in the plane;
   wherein the signal sensor further comprises:
   an optical fiber for communicating light emitted by the signal source;
   a light detector for detecting light communicated through the optical fiber; and
   wherein the asymmetrical signal means further comprises transmission loss means, including a modified upper surface of the optical fiber, for increasing transmission loss of light being communicated through the optical fiber when the fiber is bent.

2. The motion sensor according to claim 1 wherein the optical fiber is disposed between the signal source and the light detector.

3. The motion sensor according to claim 1 wherein both the signal source and the light detector are disposed on one end of the optical fiber and further comprising a reflecting means, disposed on the other end of the optical fiber for reflecting light emitted by the signal source so that the reflected light is communicated back to the light detector by the optical fiber.

4. A motion sensor comprising:
an electromagnetic signal source for emitting electromagnetic radiation;
an electromagnetic signal sensor for sensing the electromagnetic radiation from the signal source, the signal source and signal sensor being positioned on a physical body which moves symmetrically in a plane with respect to an axis, and the signal sensor ordinarily providing a symmetrical output signal indicating the continuous extent of movement of the body in the plane when the body moves symmetrically relative to the axis in the plane, the signal sensor including an optical fiber for communicating light emitted by the signal source; and
asymmetrical signal means, associated with the signal sensor, for causing the signal sensor to emit an asymmetrical output signal indicating movement in the plane in response to symmetrical movement of the body relative to the axis in the plane, the asymmetrical signal means comprising transmission loss means including a modified upper surface of the optical fiber, for the optical fiber when the fiber is bent in the plane.

5. The motion sensor according to claim 4 wherein the upper surface of the optical fiber is abraded for forming the transmission loss means.

6. The motion sensor according to claim 4 wherein the upper surface of the optical fiber has a notch for forming the transmission loss means.

7. A motion sensor comprising:
an electromagnetic signal source for emitting electromagnetic radiation;
an electromagnetic signal sensor for sensing the electromagnetic radiation from the signal source, the signal source and signal sensor being positioned over a joint of a body which pivots symmetrically in a plane with respect to an axis, and the signal sensor ordinarily providing a symmetrical output signal indicating the continuous extent of movement of the body in the plane when the body pivots symmetrically relative to the axis in the plane;
asymmetrical signal means, associated with the signal source and signal sensor, for causing the signal sensor to emit an asymmetrical output signal indicating movement in the plane in response to symmetrical pivoting of the body relative to the axis in the plane;
wherein the electromagnetic radiation emitted by the signal source and sensed by the signal sensor is visible light; and
wherein the signal sensor further comprises a flexible tube disposed in close proximity to a part of the body for bending in response to movement of the body, and wherein the asymmetrical signal means comprises setting means, disposed between the tube and the body, for setting the tube in a prescribed orientation when the body is in a prescribed position.

8. The motion sensor according to claim 7 wherein the tube is disposed on a pivoting junction between first and second members of the body so that the tube bends when the first and second members pivot relative to each other.

9. A motion sensor comprising:

an electromagnetic signal source for emitting electromagnetic radiation;
an electromagnetic signal sensor for sensing the electromagnetic radiation from the signal source, the signal source and signal sensor being positioned on a physical body which moves symmetrically with respect to an axis, and the signal sensor ordinarily providing a symmetrical output signal indicating the continuous extent of movement of the body when the body moves symmetrically relative to the axis, the signal sensor including a flexible tube disposed over a pivoting junction between first and second members of the body for communicating electromagnetic radiation from the signal source to the signal sensor and for bending in response to movement of the first and second members; and
asymmetrical signal means, associated with the signal sensor, for causing the signal sensor to emit an asymmetrical output signal in response to symmetrical movement of the first and second members relative to the axis, the asymmetrical signal means comprising:
setting means, disposed between the tube and the body, for setting the tube in a prescribed orientation when the first and second members are in a prescribed position, the setting means including a wedge disposed between the tube and the junction.

10. The motion sensor according to claim 9 wherein the first and second members are capable of pivoting symmetrically with respect to a boundary, the pivoting on one side of the boundary being termed the normal field of movement, and the pivoting on the other side of the boundary being termed the null field of movement, and wherein the wedge sets the tube generally straight when the first and second members are positioned in the null field.

11. A motion sensor comprising:
an electromagnetic signal source for emitting electromagnetic radiation;
an electromagnetic signal sensor for sensing the electromagnetic radiation from the signal source, the signal source and signal sensor being positioned on a physical body which moves symmetrically with respect to an axis so that movement of the body causes the signal source and signal sensor to move relative to each other; and
guide means for facing the light emitted by the signal source toward the signal sensor when the signal source and signal sensor move relative to each other, the guide means including an optical fiber connected to one of the signal source or signal sensor, the optical fiber having a free end facing the other of the signal source or signal sensor.

12. The motion sensor according to claim 11 wherein the guide means further comprises a tube disposed between the signal source and signal sensor, the free end of the optical fiber being disposed within the tube.

13. The motion sensor according to claim 12 wherein the optical fiber is connected to the signal source and the tube is connected to the signal sensor.

14. The motion sensor according to claim 12 wherein the optical fiber is connected to the signal sensor and the tube is connected to the signal source.

15. The motion sensor according to claim 12 wherein the free end of the optical fiber moves away from the facing signal source or signal sensor when the body moves in a prescribed direction.

16. The motion sensor according to claim 15 wherein the signal source and signal sensor are disposed across a pivoting junction between first and second members of the body, the first and second members being capable of pivoting symmetrically with respect to an axis, the pivoting on one side of the axis being termed the normal field of movement, and the pivoting on the other side of the axis being termed the null field of movement, and wherein the free end of the optical fiber moves away from the facing signal source or signal sensor when the first and second members pivot away from the axis in the normal field of movement.

17. The motion sensor according to claim 16 wherein the free end of the optical fiber moves toward the facing signal source or signal sensor when the first and second members pivot away from the axis in the null field of movement.

18. A motion sensor comprising:
an electromagnetic signal source for emitting electromagnetic radiation;
an electromagnetic signal sensor for sensing the electromagnetic radiation from the signal source, the signal source and signal sensor being disposed proximate a physical body so that movement of the body causes the signal source and signal sensor to move relative to each other; and
guide means for directing the electromagnetic radiation emitted by the signal source toward the signal sensor when the signal source and signal sensor move relative to each other, the guide means including a radiation conduit coupled to one of the signal source of signal sensor, the conduit having a free end facing the other of the signal source or signal sensor.

19. The motion sensor according to claim 18 wherein the electromagnetic radiation is light, and wherein the conduit is an optical fiber.

20. The motion sensor according to claim 19 wherein the guide means further comprises a tube disposed between the signal source and signal sensor, the free end of the optical fiber being disposed within the tube.

21. The motion sensor according to claim 20 wherein the signal source and signal sensor are disposed across a pivoting junction between first and second members of the body, the first and second members being capable of pivoting symmetrically with respect to an axis, the pivoting on one side of the axis being termed the normal field of movement, and the pivoting on the other side of the axis being termed the null field of movement, and wherein the free end of the optical fiber moves away from the facing signal source or signal sensor when the first and second members pivot away from the axis in the normal field of movement.

22. The motion sensor according to claim 21 wherein the free end of the optical fiber moves toward the facing signal source or signal sensor when the first and second members pivot away from the boundary in the null field of movement.

23. The motion sensor according to claim 21 further comprising stop means for preventing the free end of the optical fiber from moving toward the facing signal source or signal sensor when the first and second members pivot away from the boundary in the null field of movement.

24. A method for indicating movement of first and second body segments which are coupled to each other through a pivot point and which pivot symmetrically in a plane with respect to an axis, comprising the steps of:
emitting electromagnetic radiation with a signal source associated with the first body segment;
communicating the electromagnetic radiation from the signal source and across the pivot point through an electromagnetic radiation conduit;
sensing the communicated electromagnetic radiation with a signal sensor;
disposing a wedge between the conduit and the pivot point; and
emitting an asymmetrical output signal indicating the continuous extent of movement of the first and second body segments in the plane in response to symmetrical pivoting of the first and second body segments relative to the axis in the plane.

25. The method according to claim 24 wherein the conduit comprises a first medium adjacent to a second medium, and further comprising the steps of:
communicating the electromagnetic radiation through the first medium;
reflecting the electromagnetic radiation from an interface between the first medium and the second medium for maintaining the propagation of electromagnetic radiation through the first medium.

26. The method according to claim 25 wherein the electromagnetic radiation is visible light.

27. A method for indicating movement of first and second body segments which are coupled to each other through a pivot point and which pivot symmetrically in a plane with respect to an axis, comprising the steps of:
emitting electromagnetic radiation with a signal source associated with the first body segment;
communicating the electromagnetic radiation from the signal source and across the pivot point through an optical fiber;
sensing the communicated electromagnetic radiation with a signal sensor;
pivoting the optical fiber symmetrically when the first and second body segments pivot symmetrically relative to the axis;
modifying an upper surface of the optical fiber;
increasing transmission loss through the upper surface of the optical fiber when the optical fiber pivots to one side of the pivot point; and
emitting an asymmetrical output signal indicating the continuous extent of movement of the first and second body segments in the plane in response to symmetrical pivoting of the first and second body segments relative to the axis in the plane.

28. The method according to claim 27 wherein the modifying step further comprises the step of abrading the upper surface of the optical fiber.

29. The method according to claim 27 wherein the modifying step further comprises the step of etching the optical fiber.

30. A method for indicating movement of first and second body segments which are coupled to each other through a pivot point and which pivot symmetrically in a plane with respect to an axis, comprising the steps of:
emitting electromagnetic radiation with a signal source associated with the first body segment;
communicating the electromagnetic radiation from the signal source and across the pivot point through an electromagnetic radiation conduit;
sensing the communicated electromagnetic radiation with a signal sensor;
connecting the radiation conduit for movement with one of the signal source or signal sensor;

facing a free end of the radiation conduit toward the other of the signal source or signal sensor; and emitting an asymmetrical output signal indicating the continuous extend of movement of the first and second body segments in the plane in response to symmetrical pivoting of the first and second body segments relative to the axis in the plane.

31. The method according to claim 30 further comprising the step of asymmetrically moving the free end of the radiation conduit relative to the facing signal source or signal sensor when the first and second body segments pivot relative to the pivot point.

32. The method according to claim 31 wherein the radiation communicating step further comprises the step of communicating the electromagnetic radiation through an optical fiber.

33. A motion sensor comprising:

an electromagnetic signal source for emitting electromagnetic radiation;

an electromagnetic signal sensor for sensing the electromagnetic radiation from the signal source, the signal source and signal sensor being positioned on a physical body which moves symmetrically in a plane with respect to an axis, and the signal sensor ordinarily providing a symmetrical output signal indicating the continuous extent of movement of the body in the plane when the body pivots symmetrically relative to the axis in the plane, the signal sensor including an optical fiber for communicating light emitted by the signal source; and asymmetrical signal means, associated with the signal sensor, for causing the signal sensor to emit an asymmetrical output signal indicating movement in the plane in response to symmetrical movement of the body about the axis in the plane, the asymmetrical signal means comprising transmission loss means disposed on an upper surface of the optical fiber, for increasing transmission loss of light being communicated through the optical fiber only when the fiber is bent in the plane.

34. A motion sensor comprising:

an electromagnetic signal source for emitting electromagnetic radiation;

an electromagnetic signal sensor for sensing the electromagnetic radiation from the signal source, the signal source and signal sensor being positioned on a physical body which pivots symmetrically in a plane with respect to an axis, and the signal sensor ordinarily providing a symmetrical output signal indicating the continuous extent of movement of the body in the plane when the body pivots symmetrically relative to the axis in the plane, the signal sensor including a flexible radiation conduit disposed over a pivoting junction between first and second members of the body for communicating electromagnetic radiation from the signal source to the signal sensor and for bending in response to movement of the first and second member;

wherein the radiation conduit comprises a first medium adjacent to a second medium so that electromagnetic radiation propagates through the first medium and is at least in part reflected from an interface between the first medium and the second medium for maintaining the propagation of electromagnetic radiation through the first medium;

asymmetrical signal means, associated with the signal sensor, for causing the signal sensor to emit an asymmetrical output signal in response to symmetrical movement of the first and second members, the asymmetrical signal means comprising:

setting means, disposed between the radiation conduit and the body, for setting the radiation conduit in a prescribed orientation when the body is in a prescribed position, the setting means including a wedge disposed between the radiation conduit and the junction.

35. The motion sensor according to claim 34 wherein the first and second members are capable of pivoting symmetrically relative to the axis, the pivoting on one side of the axis being termed the normal field of movement, and the pivoting on the other side of the axis being termed the null field of movement, and wherein the wedge sets the conduit generally straight when the first and second members are positioned in the null field.

36. The motion sensor according to claim 35 wherein the electromagnetic radiation comprises visible light.

* * * * *